US009951295B2

(12) United States Patent
Haught et al.

(10) Patent No.: US 9,951,295 B2
(45) Date of Patent: Apr. 24, 2018

(54) COMPOSITIONS FOR DEPOSITION ON BIOLOGICAL SURFACES (71) Applicant: The Procter & Gamble Company, Cincinnati, OH (US)

(72) Inventors: John Christian Haught, West Chester, OH (US); William Michael Glandorf, Mason, OH (US); Steven Hamilton Hoke, West Chester, OH (US); Victor Manuel Arredondo, West Chester, OH (US); Peter Yau Tak Lin, Liberty, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 14/626,421

(22) Filed: Feb. 19, 2015

(65) Prior Publication Data

US 2016/0244695 A1    Aug. 25, 2016

(51) Int. Cl.
*C11C 3/00* (2006.01)
*A61K 8/37* (2006.01)
*A61K 8/60* (2006.01)
*A61Q 11/00* (2006.01)

(52) U.S. Cl.
CPC ............... *C11C 3/003* (2013.01); *A61K 8/37* (2013.01); *A61K 8/60* (2013.01); *A61Q 11/00* (2013.01)

(58) Field of Classification Search
CPC .......... C11C 3/003; A61Q 11/00; A61K 8/60; A61K 8/37
USPC .................................... 424/49, 435
See application file for complete search history.

(56) References Cited

U.S. PATENT DOCUMENTS

| | | |
|---|---|---|
| 2,946,725 A | 7/1960 | Norris et al. |
| 3,111,127 A | 11/1963 | Jarboe |
| 3,535,421 A | 10/1970 | Briner et al. |
| 3,538,230 A | 11/1970 | Pader et al. |
| 3,678,154 A | 7/1972 | Widder et al. |
| 3,862,307 A | 1/1975 | Di Giulio |
| 3,917,613 A | 11/1975 | Humbert et al. |
| 3,991,178 A | 11/1976 | Humbert et al. |
| 4,029,759 A | 6/1977 | Humbert et al. |
| 4,051,234 A | 9/1977 | Gieske et al. |
| 4,070,496 A | 1/1978 | Rowsell et al. |
| 4,150,052 A | 4/1979 | Watson et al. |
| 4,136,163 A | 5/1979 | Rowsell et al. |
| 4,153,679 A | 5/1979 | Rowsell et al. |
| 4,157,384 A | 6/1979 | Browning et al. |
| 4,178,459 A | 12/1979 | Rowsell et al. |
| 4,206,215 A | 6/1980 | Bailey |
| 4,230,688 A | 10/1980 | Roswell et al. |
| 4,340,583 A | 7/1982 | Wason |
| 4,459,425 A | 7/1984 | Amano et al. |
| 4,496,322 A | 1/1985 | Sandham et al. |
| 4,512,743 A | 4/1985 | Santucci et al. |
| 4,883,534 A | 11/1989 | Sandham et al. |
| 4,894,220 A | 1/1990 | Gaffar et al. |
| 5,004,597 A | 4/1991 | Majeti et al. |
| 5,015,466 A | 5/1991 | Parran et al. |
| 5,180,577 A | 1/1993 | Polefka et al. |
| 5,266,592 A | 11/1993 | Grueb et al. |
| 5,281,410 A | 1/1994 | Lukacovic et al. |
| 5,430,074 A | 7/1995 | Barnes et al. |
| 5,451,404 A | 9/1995 | Furman |
| 5,578,293 A | 11/1996 | Prencipe et al. |
| 5,589,160 A | 12/1996 | Rice et al. |
| 5,603,920 A | 2/1997 | Rice |
| 5,608,119 A | 3/1997 | Amano et al. |
| 5,651,958 A | 7/1997 | Rice |
| 5,658,553 A | 8/1997 | Rice |
| 5,703,123 A | 12/1997 | Pelzer et al. |
| 5,716,601 A | 2/1998 | Rice |
| 5,725,865 A | 3/1998 | Mane et al. |
| 5,800,848 A | 9/1998 | Yatka et al. |
| 5,843,466 A | 12/1998 | Mane et al. |
| 5,977,166 A | 11/1999 | Greenberg |
| 6,036,494 A | 3/2000 | Cohen |
| 6,365,215 B1 | 4/2002 | Grainger et al. |
| 6,451,844 B1 | 9/2002 | Watkins et al. |
| 6,524,559 B2 | 2/2003 | Urai et al. |
| 6,592,884 B2 | 7/2003 | Hofmann et al. |
| 6,884,903 B2 | 4/2005 | Lorenz et al. |
| 6,956,139 B2 | 10/2005 | Green et al. |
| 7,189,760 B2 | 3/2007 | Erman et al. |
| 8,679,569 B2 | 3/2014 | Appleby et al. |
| 8,808,784 B2 | 8/2014 | Lin et al. |
| 2011/0076241 A1 | 3/2011 | Kato et al. |
| 2011/0089073 A1* | 4/2011 | Baig .................. A61K 8/24 206/524.1 |
| 2011/0257030 A1* | 10/2011 | Stella .................. A61K 8/03 506/9 |
| 2012/0328763 A1* | 12/2012 | Lin .................. A23D 7/011 426/606 |
| 2012/0330000 A1 | 12/2012 | Lin et al. |
| 2013/0149273 A1* | 6/2013 | Wei .................. A61K 8/73 424/70.13 |

FOREIGN PATENT DOCUMENTS

| | | |
|---|---|---|
| EP | 310299 | 4/1989 |
| GB | 1315626 | 5/1973 |
| WO | WO200222096 | 3/2002 |
| WO | WO2005049553 A1 | 6/2005 |
| WO | WO2006103401 | 10/2006 |

* cited by examiner

*Primary Examiner* — Yih-Horng Shiao
(74) *Attorney, Agent, or Firm* — James E. Oehlenschlager (57) ABSTRACT A sucrose polyester composition that imparts a coating providing a slickness to teeth when delivered from an oral care composition.

13 Claims, 2 Drawing Sheets

FIG. 1

| Sample Coating | ΔL |
|---|---|
| A Dentifrice only (no Sefa) | |
| B (Cottonseed Olean) | |
| C (DairyLean Olean) | |
| D (Sefose 2275) | |
| E (Sefa Soyate IV40) | |
| F (Sefa Soyate LP 426) | |
| G (Butterlean Olean) | |
| H (Sefa Soyate) | |
| I (Soybean Olean) | |
| J Sefa Soyate IMF40 | |
| No treatment (HAP only)- | |
| No stain blank filter paper | |

Tea stain photos – Dentifrice Treatments
FIG. 2

COMPOSITIONS FOR DEPOSITION ON BIOLOGICAL SURFACES

FIELD OF THE INVENTION

The present invention relates to a composition comprising sucrose polyesters to deliver a sensation of coating and/or stain prevention.

BACKGROUND OF THE INVENTION

Oral Care products that coat tooth surfaces can provide stain prevention, protection from bacterial and food acids, and a sensorial benefit of tooth slickness or perception surface smoothness.

Prevention of dental caries by coating a tooth with a casein phosphopeptide-amorphous calcium phosphate complex was disclosed in US Pub. No. 2011/0076241. Though they were able to show tooth coating, they had to deliver the material from a water-free composition, thus imposing a barrier to delivery from a toothpaste. In the presence of water, they were unable to deliver a stable film to the tooth's surface and thus were required to have a non-aqueous composition.

Coating the teeth with an antimicrobial varnish (U.S. Pat. No. 4,883,534, and U.S. Pat. No. 4,496,322) or preventative resin has been a means to combat dental caries by a variety of technologies, such as shellac resin (U.S. Pat. No. 6,524,559) or a methacrylate resin to repair caries lesions (U.S. Pat. No. 5,430,074). The inventions related to these coating compositions have to be delivered from a solvent based system that is brushed on, where the resin is the residual after the solvent dries.

For aesthetic purposes, teeth have been coated with reactive glass ionomers (U.S. Pat. No. 6,036,494) or etching the teeth to deliver a non-removable polymer (U.S. Pat. No. 4,512,743). A coating composition is needed that can be added to oral care products, so the composition can be applied to the teeth during a user's normal oral care product usage.

SUMMARY OF THE INVENTION

An oral care composition is provided that comprises sucrose polyester.

In certain embodiments an oral care composition may have at least one of a HAP particle absorption rate of about 55% or less or from about 35% to about 55% for deionized water, about 70% or less for toluene, or 70% or less for xylene.

In certain embodiments an oral care composition may have at least one of a percent flow of solvent rate of about 35% or greater or from about 35% to about 55% for deionized water, or from about 20% or greater or from about 20% to about 40% for toluene, or from about 30% or greater or from about 30% to about 50% for xylene.

In certain embodiments an oral care composition may have a sucrose polyester deposition measurement of from about 300 µg/g of HAP to about 800 µg/g of HAP, or from about 500 µg/g of HAP to about 1100 µg/g of HAP, or at least about 340 µg/g of HAP, or at least about 500 µg/g of HAP, as measured by the HAP particle deposition method.

In certain embodiments an oral care composition may have a tea stain ΔE when applied to a HAP surface of about 15 to about 25, or from about 17 to about 21, or from about 21, or from about 18 or less.

In certain embodiments of an oral care composition the sucrose ester may have a solids fat content of at least about 10% to about 99% at 10° C., or from about 40% to about 70% at 10° C., or at least about 40% at 10° C.

In certain embodiments of an oral care composition the sucrose ester may have a solids fat content of at least about 10% to about 99% at 10° C., or from about 40% to about 70% at 10° C., or at least about 40% at 10° C. and at least about from about 5% to about 99% at 40° C., or from about 5% to about 40% at 40° C. In certain embodiments of an oral care composition the sucrose ester may have a solids fat content of at least about 40% at 10° C. and at least 5% at 40° C.

An oral care composition comprising a sucrose ester is provided wherein the oral care composition comprises a HAP particle absorption rate of about 55% or less for deionized water; a HAP particle deionized water flow rate of about 35% or greater; has a sucrose polyester deposition measurement of at least about 340 µg per g of HAP, as measured by the HAP particle deposition method; and wherein the sucrose ester has a solids fat content of at least about 40% at 10° C.

DETAILED DESCRIPTION OF THE INVENTION

The tooth surface structure includes a fluoro-hydroxyapatite matrix (calcium-phosphate-hydroxy-fluoride), which has the property of attracting anionic molecules. A close mimic to the fluoro-hydroxyapatite is synthesized hydroxyapatite or HAP, which can be used to mimic the interaction of substances on the tooth surface. Sucrose polyesters are one such class of anionic molecules that are weakly attracted to the tooth surface, thus allowing for the perception of coating by the consumer. Sucrose polyesters ("SPE"), typically used as fat substitutes in food products, as described in US Pub. No. 2012/0330000, provide surprisingly noticeable tooth coating characteristics. Surprisingly, only three SPE's have the desirable tooth feel attributes and reduction of stain build up on the teeth. The invention described herein includes compositions containing SPE's, such as Sefose 2275, Sucrose Ester Fatty Acid (SEFA) soyate IV40, or Cottonseed Olean, and their applications to deliver tooth feel and protection.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

As used herein, the word "or" when used as a connector of two or more elements is meant to include the elements individually and in combination; for example X or Y, means X or Y or both.

By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include hair coloring compositions, oral care compositions, after shave gels and creams, pre-shave preparations, shaving gels, creams, or foams, moisturizers and lotions, cough and cold compositions, leave-on skin lotions and creams, shampoos, conditioners, shower gels, bar soaps, toilet bars, antiperspirants, deodorants, depilatories, lipsticks, foundations, mascara, sunless tanners and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "teeth", as used herein, refers to natural teeth as well as artificial teeth or dental prosthesis.

Sucrose polyesters (SPE), because of their bulk and shape, form crystalline structures having melting profiles that are quite dissimilar to certain natural fats and oils. Sucrose polyesters have a very flat melting profile across a broad temperature range. By fully hydrogenating sucrose polyesters, it is possible to increase the melting point by converting sucrose polyesters containing unsaturated carbon chains into sucrose polyesters containing saturated carbon chains; however, the melting profile of such sucrose polyesters remains flat, resulting in a high solids content at body temperatures (approximately 37° C.). When these fully hydrogenated sucrose polyesters are incorporated into food products, such high solids content causes an undesirable, waxy mouth feel for the consumer eating the food product. This is particularly disadvantageous when the sucrose polyesters are incorporated into cheese, chocolate or other confections; as such products are favored by the consumer, in part, due to a particular mouth feel associated with these types of products. In other words, certain food products (e.g., cheese, chocolates, frostings, icings, ice creams, etc.) may be particularly preferred because of the products' ability to melt in a consumer's mouth. These same characteristics that make an SPE undesirable for foods are advantageous for oral care products, since the high melting points would favor deposition on the tooth surface when delivered from a dentifrice or mouthwash. An example of a sucrose polyester that may be used in the present invention is shown below:

R is independently selected from:
i. COR' (ester group)
ii. H

Where R' is an alkyl group from about 7 to about 25 carbon atoms.

Blends of different polyol fatty acid polyesters, for example a solid and liquid, can be used to dial in viscosity, "mouth feel" and "mouth coating" characteristics. These blends can be characterized by measuring the solid fat content (SFC) profile across a temperature range, for example from typical room temperature to body temperature or above. Determination of SFC values over a range of temperatures can be done by a method involving PNMR (pulsed NMR). Such a method is well known to those skilled in the art (see J. Amer. Oil Chem. Soc., Vol 55 (1978), pp 328-31, and Official Methods and Recommended Practices of the American Oil Chemists Society). TABLE 1 shows the solid fat content of some sucrose polyesters that may be used in the invention.

TABLE 1

| | Samples with SFC (%) per temp (° C.) | | | | | |
|---|---|---|---|---|---|---|
| Temp in C.° | SEFA Soyate | SEFA Behenate | SEFA Soyate IMF 40 | ButterLean Olean | DairyLean Olean | Soybean Olean |
| 10 | 5.3 | 99.0 | 86.5 | 44.3 | 64.4 | 10.8 |
| 20 | 2.1 | 99.0 | 75.6 | 11.3 | 45.9 | 7.6 |
| 25 | 1.5 | 99.0 | 66.4 | 9.2 | 31.8 | 7.0 |
| 30 | 0.9 | 99.0 | 57.2 | 7.0 | 17.6 | 6.4 |
| 35 | 0.5 | 99.0 | 48.4 | 6.2 | 11.1 | 6.0 |
| 40 | 0.1 | 99.0 | 39.5 | 5.4 | 5.5 | 5.6 |

Sucrose polyesters, which include Olean derivatives, are defined as Polyol Fatty Acid Polyesters (e.g. Sucrose Ester of Fatty Acids). The polyol fatty acid polyesters comprise well-defined polyol fatty acid esters.

The polyol starting material may have at least two esterifiable hydroxyl groups. Examples of suitable polyols are sugars, especially monosacharides and disaccharides, and sugar alcohols. Examples of monosaccharides containing four hydroxyl groups are xylose and arabinose and the sugar alcohol derived from xylose, i.e. xylitol. Suitable five hydroxyl group-containing monosaccharides are galactose, fructose and sorbose. Sugar alcohols containing six hydroxyl groups derived from sucrose, glucose and sorbose, e.g. sorbitol, are also suitable. Examples of disaccharide polyols which can be used include maltose, lactose, trehalose, raffinose, and sucrose, all of which contain eight or more hydroxyl groups. Examples of polyol esters for use in the present invention include erythritol, xylitol, sorbitol, glucose and sucrose.

Polyols can be esterified with a fatty acid having from about 8 to about 26 carbon atoms or from about 12 to about 22 carbon atoms. Examples of such fatty acids include caprylic, capric, lauric, myristic, myristoleic, palmitic, palmitoleic, stearic, oleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers, depending on the desired physical properties, for example liquid or solid, of the polyol fatty acid ester compound. The fatty acid ester groups can be the same or mixed on the same sugar or sugar alcohol molecule.

Naturally occurring fats and oils can serve as the source for the fatty acid component in the sugar or sugar alcohol fatty acid ester. For example, grapeseed oil is a good source of C20-22 fatty acids; soybean oil, cottonseed oil and tallow provide a good source of C16-C18 fatty acids. Shorter chain fatty acids can be provided by coconut, palm kernel, or babassu oils. Corn oil, lard, olive oil, and sunflower seed oil, are examples of other natural oils which can serve as the source of the fatty acid component.

It is not necessary that all of the hydroxyl groups of the sugar or sugar alcohol be esterified with fatty acid, but in certain embodiments the compound may contain no more than 2 unesterified hydroxyl groups. In still other embodiments, all of the hydroxyl groups of the sugar or sugar alcohol are esterified with fatty acid, i.e. the compound is substantially completely esterified.

Sucrose polyesters include, sucrose polyester derivatives, such as Sucrose Ester Fatty Acids (SEFA's), which are composed of varying degrees of esterification and varying chain lengths of fatty acids, examples of which include, SEFA Soyate, SEFA Cottonate, SEFA Soyate IMF40, SEFA Behenate (aka Sefose 2275), SEFA Soyate LP426, Palm Stearin SPE. Olean® is the brand name for different Olestra compositions. Olestra is the common name for sucrose polyester FDA approved. Every Olean is a blend of 2 sucrose polyesters: Cottonseed Olean=SEFA Cottonate+ SEFA Behenate; Soybean Olean=SEFA Soyate+SEFA Behenate; ButterLean Olean=SEFA Soyate LP426+SEFA Behenate; DairyLean=Palm Stearin SPE+SEFA Behenate. SEFA Soyate IV40=Sucrose octa-ester+sucrose hepta-ester. These Oleans are made by fully melting both components and then letting the mixture cool to ambient temperature.

These Oleans are described in greater detail in U.S. Pat. No. 8,808,784 B2 assigned to Procter & Gamble.

In certain embodiments, oral care compositions may comprise from about 0.0001% to about 20% sucrose polyesters, by total weight percent or from about 0.001% to about 5%, by total weight percent.

The oral care compositions of the present invention may include one or more of the following components, which can include metal salts, sweeteners, carrier materials, antimicrobial agents, bad breath reduction agents, bleaching agents (hydrogen peroxide), surfactants, flavors (menthol), anti-tartar agents, colorants, sensates, abrasive polishing materials, thickening materials, humectants, and other additives.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

A metal salt includes zinc salts, stannous salts, potassium salts, copper salts, alkali metal bicarbonate salts, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the oral care composition.

It is common to have a fluoride compound present in dentifrices and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 and U.S. Pat. No. 3,678,154.

Stannous salts include stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597. Other descriptions of stannous salts are found in U.S. Pat. No. 5,578,293 and in U.S. Pat. No. 5,281,410. In addition to the stannous ion source, other ingredients used to stabilize the stannous may be included, such as the ingredients described in U.S. Pat. No. 5,004,597 and U.S. Pat. No. 5,578,293.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

In certain embodiments, the copper salt is selected from copper fluoride, copper chloride, copper iodide, copper chlorofluoride, copper acetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt is selected from copper gluconate, copper acetate, copper glycinate, and combinations thereof.

Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. Because of the pH at which alkali metal bicarbonate salts buffer, the bicarbonate salt may be in a phase separate from the stannous ion source. In certain embodiments, the oral care composition of the present invention may contain from about 0.5% to about 50%, from about 0.5% to about 30%, from about 2% to about 20%, or from about 5% to about 18% of an alkali metal bicarbonate salt, by weight of the oral care composition.

Sweeteners include saccharin, steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana is a steviolglycoside from Cargill Corp., Minneapolis, Minn., which is an extract from the leaves of the Stevia rebaudiana plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside E, rebaudioside F, stevioside, steviolbioside, dulcoside A. Sweeteners are generally included in an oral care composition at a level of about 0.0005% to about 2%, by total weight of the oral care composition.

Carrier materials include water, glycerin, sorbitol, polyethylene glycols having a molecular weight of less than about 50,000, propylene glycol and other edible polyhydric alcohols, ethanol, or combinations thereof. The oral compositions of the present invention include from about 5% to about 80%, by weight of the composition, of a carrier material. In certain embodiments, the compositions contain carrier materials in an amount of from about 10% to about 40%, by total weight of the oral care composition.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium]alkanes as disclosed in U.S. Pat. No. 4,206,215 and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725 and in U.S. Pat. No. 4,051,234. Examples of other antimicrobial agents include chlorhexidine, triclosan, triclosan monophosphate, and flavor oils such as thymol. Triclosan and other agents of this type are disclosed in U.S. Pat. No. 5,015,466 and U.S. Pat. No. 4,894,220.

Of the above antimicrobial agents, examples of some, which provide an unwanted taste, include, for example, chlorhexidine, triclosan, and thymol. The unwanted tastes often associated with these types of antimicrobial agents include bitter, dirty, earthy, sour, and/or astringent.

The compositions of the present invention may contain antimicrobial agents in an amount of from about 0.035% or more, from about 0.1% to about 1.5%, from about 0.045% to about 1.0%, or from about 0.05% to about 0.10%, by total weight of the oral care composition.

The compositions of the present invention may contain bad breath reduction agents in an amount of from about 0.001% to about 4.0%, by total weight of the oral care composition.

Bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. Some bleaching agents provide a burn sensation within an oral care composition, for example peroxides and percarbonates.

The compositions of the present invention may contain bleaching agents in an amount of from about 0.01% to about 30%, from about 0.1% to about 10%, or from about 0.5% to about 5%, by total weight of the oral care composition.

Surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

Some other organophosphate agents include alkyl or alkenyl phosphate esters represented by the following structure:

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b- group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these surfactants are soapy, bitter, chemical, or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 and/or TRPV1 agonists.

Cationic surfactants useful in the present invention include derivatives of quaternary ammonium compounds having one long alkyl chain containing from about 8 to 18 carbon atoms such as lauryl trimethylammonium chloride, cetyl pyridinium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic surfactants can also act as germicides in the oral care compositions disclosed herein.

Examples of some flavors and flavor components that may be used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors are generally present in an amount of from about 0.4% to about 5% or from about 1% to about 3%, by total weight of the oral care composition.

Anti-tartar agents include pyrophosphate salts as a source of pyrophosphate ion. The pyrophosphate salts useful in the present compositions include, for example, the mono-, di- and tetraalkali metal pyrophosphate salts and combinations thereof. Disodium dihydrogen pyrophosphate (Na2H2P2O7), sodium acid pyrophosphate, tetrasodium pyrophosphate (Na4P2O7), and tetrapotassium pyrophosphate (K4P2O7) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt may be from about 1.5% to about 15%, from about 2% to about 10%, or about 3% to about 8%, by total weight of the oral care composition.

Examples of some colorants that may be used in oral care compositions include D&C Yellow No. 10, FD&C Blue No.

1, FD&C Red No. 40, D&C Red No. 33 and combinations thereof. In certain embodiments, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the consumer. Sensates are generally present in an amount of from about 0.001% to about 0.8%, by weight of the oral care composition. The most well-known cooling sensate compound is menthol, particularly L-menthol, which is found naturally in peppermint oil notably of Mentha arvensis L and Mentha viridis L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there is no cooling effect for the other isomers. For example, d-neomenthol is reported to have a cooling threshold of about 25,000 ppb and 1-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201].

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,5703,123; 5,725,865; 5,843,466; 6,365,215; 6,451,844; and 6,884,903. Ketal derivatives, such as those described in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112 and phosphine oxides as reported in U.S. Pat. No. 4,070,496. Of these cooling sensates, some provide an unwanted taste, for example, menthol and menthone.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain embodiments, if the oral composition or particular phase comprises a polyphosphate having an average chain length of about 4 or more, calcium containing abrasives and alumina are not preferred abrasives.

Silica dental abrasives of various types are often used in oral care compositions due to their exceptional dental cleaning and polishing performance without unduly abrading tooth enamel or dentine. Silica abrasive polishing materials that may be used in the present invention, as well as other abrasives, generally have an average particle size ranging between about 0.1 to about 30 µm or from about 5 to about 15 µm. The abrasive can be precipitated silica or silica gels such as the silica xerogels described in U.S. Pat. No. 3,538,230 and U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. No. 4,340,583; and U.S. Pat. Nos. 5,589,160; 5,603,920; 5,651,958; 5,658,553; and 5,716,601.

Thickening material or binders may be used to provide a desirable consistency to the oral care compositions of the present invention. For example, when the oral care compositions are in the form of toothpastes, dentifrices, topical oral gels, mouthrinse, denture product, mouthsprays, lozenges, oral tablets or chewing gums, the amount and type of the thickening material will depend upon the form of the product. Thickening materials include carboxyvinyl polymers, carrageenan, hydroxyethyl cellulose, and water soluble salts of cellulose ethers, such as sodium carboxymethylcellulose and sodium hydroxyethyl cellulose. Natural gums, such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition.

Humectants keep oral care compositions from hardening upon exposure to air and certain humectants can also impart desirable sweetness of flavor to toothpaste compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

EXAMPLES

Example 1: Method to Determine Sucrose Polyester Coating of Hydroxyapatite

Hydroxyapatite (HAP) was used as a model of the tooth surface to determine the effectiveness of sucrose polyesters in forming a coating. Hydroxyapatite (HAP, Biorad Bio-gel #130-0421) powder (1 gram), was added to a 50 ml conical centrifuge tube, which contained 20 ml of deionized water at room temperature (~68° F.). The HAP water solution was vortexed for 30 seconds and then centrifuged for 15 minutes at 15,000 rpm to precipitate the washed HAP. The water was decanted and the procedure was repeated three more times. The pellet after the fourth wash was resuspended in 5-10 ml of deionized water and vortexed for 30 seconds. This solution was poured onto a Millipore filter disk (Millipore MF membrane filter 4.5 µm, 47 mm diameter, catalog #HAWP04700) in a vacuum filter apparatus. The disk was dried for two days at room temperature (25° C.). The powder was collected by scraping off the filter disk into a collection vial.

The sucrose polyester solution was prepared by adding 1 gram of sucrose polyester from Table 1 to 3 grams of menthol, and 92 grams of water. This solution was stirred in a 250 ml beaker for 10 minutes at 45° C. After 10 minutes, 4 grams of poloxamer 407 was slowly added and the mixture continued stirring for 30 minutes at 45° C. This solution was then used to test for coating of the HAP particles.

Flow Through Test

One gram of the dried coated HAP particles was then packed into a 5 ml syringe (5 ml BD Luer-Lock disposable syringe with 1/10 mL graduation). The weight of the syringe plus particles was taken. Added 2.0 ml of a solvent selected from xylene, toluene, or water as a control, to the syringe and weighed. To determine the amount of solvent that passed through the coated HAP particles over a period of 30 minutes, the solvent that passed through was weighed every 5 minutes.

TABLE 2

| Grams flow per minute through HAP coated particles | | | |
| --- | --- | --- | --- |
| Coating | HAP None | HAP Cottonseed Olean | HAP SEFA Soyate IV40 |
| | | Grams Flow Per Minute | |
| Solvent | | | |
| Water | 0.45 | 0.11 | 0.11 |
| Toluene | 1.06 | 0.22 | 0.18 |
| Xylene | 0.82 | 0.24 | 0.20 |

Water flow through the hydrophobic coated particles from Cottonseed Olean or SEFA Soyate IV40 was slowed vs. the untreated particles. The test results show that SEFA on the surface of the HAP allowed for the HAP particles to get closer to each other and thus form tight pores, as evidenced by the fluid flowing through the column.

Measuring Particle Absorption

The dried coated HAP particles (0.1 g) were then packed into a 5 ml syringe (5 ml BD Luer-Lock disposable syringe with 1/10 mL graduation). The weight of the syringe plus HAP particles was determined. Added 0.4 ml of a solvent selected from xylene, toluene, or water as a control, to the syringe and weighed. Let the solvent or water pass through the particles by gravity flow for 20 minutes and then weighed the syringe plus HAP particles and the solvent that had passed through the syringe into a collection beaker.

TABLE 3

Percentage of solvent absorbed on HAP coated vs. uncoated particles

| | % Absorbed | | |
|---|---|---|---|
| | Water | Toluene | Xylene |
| HAP (No Coating) | 72% | 75% | 72% |
| HAP (Cottonseed Olean Coating) | 54% | 65% | 63% |
| HAP (SEFA Soyate IV40 Coating) | 53% | 59% | 61% |

TABLE 3 shows the uncoated HAP particles as holding more water and solvents (toluene and xylene) than do the coated HAP particles. The percentage of solvent or water adsorbed onto the HAP was calculated by measuring the weight of the solvent or water after flowing through the syringe divided by the weight of the wet HAP after flow through. The Cottonseed Olean and Soyate IV40 coated HAP particles both held considerable less (54% & 53%) water relative to the uncoated HAP (73%). The Soyate IV40 coated HAP held less toluene than the uncoated HAP (59% vs. 75%) and the Cottonseed Olean coated HAP held less toluene than the uncoated HAP (65% vs. 75%). The Cottonseed Olean and Soyate IV40 coated HAP both held less xylene (63% and 61%) in comparison to the uncoated HAP (72%). This data shows that as the HAP became coated with either Cottonseed Olean or SEFA Soyate IV40, it held less of the hydrophilic material (water).

Measuring SPE Deposition on HAP Particles Using the HAP Particle Deposition Method A portion of the HAP particles (~0.5 g) was weighed into a glass centrifuge tube and extracted with 6 mL of toluene (99.5%+ACS grade from Sigma Aldrich, St. Louis, Mo., USA). The capped tube was placed on a roller mixer for 30 min. After that time, the solvent was removed and placed in a clean, labeled glass vial, and an additional 6 mL of toluene was added to the tube containing the HAP for a second extraction. The second extract was combined with the first extract, and both extracts were evaporated under a stream of nitrogen gas, and reconstituted with 0.4 mL of toluene. The reconstituted toluene extract containing the SPE was filtered (Nylon Acrodisc, 0.45 mm, 4 mm, Pall Corporation, Port Washington, N.Y., USA) prior to size exclusion chromatographic analysis. Separation was carried out using a Waters Alliance 2695 HPLC (Waters Corporation, Milford, Mass., USA) with two GPC columns (Waters Styragel HR1 and HR4, Waters Corporation, Milford, Mass., USA) connected in series and SPE detection was achieved using a Waters 2414 refractive index detector (Waters Corporation, Milford, Mass., USA). Quantitation of SPE concentrations in the reconstituted toluene solutions was performed against a calibration curve prepared with sefa soyate raw material.

In TABLE 4 the column labeled Toluene (g) lists the amount of toluene used to reconstitute the SPE extracted from the HAP particles and that is remaining after filtration, etc. The column Meas. SPE (µg/g) provides the concentration of SPE measured in the toluene sample that contains all of the SPE extracted from the HAP. Therefore the amount of SPE extracted from HAP in each sample=Meas. SPE (µg/g)×toluene (g); as an example 12612.85×0.3436=4333.775 total µg of SPE. Then to calculate the concentration of SPE that was deposited on [and recovered from] HAP, you divide 4333.775 total µg SPE by (1) HAP (g) 0.5567=7785 µg SPE deposition per gram of HAP.

TABLE 4

Deposition profile of the sucrose polyesters on HAP

| Description | Hap (g) | Meas. SPE (µg/g of Toluene) | Toluene containing SPE extracted from HAP (g) | SPE Deposition (µg/g HAP) |
|---|---|---|---|---|
| Sefose 2275 | 0.5567 | 12612.85 | 0.3436 | 7785 |
| SEFA Soyate IV40 | 0.5792 | 1692.29 | 0.3516 | 1027 |
| Cottonseed Olean | 0.5163 | 1242.32 | 0.3325 | 800 |
| Palm Stearin | 0.3954 | 710.26 | 0.3328 | 598 |
| Soybean Olean | 0.5338 | 551.39 | 0.3374 | 349 |
| SEFA Soyate IMF40 | 0.4959 | 497.59 | 0.3349 | 336 |
| DairyLean Olean | 0.4858 | 472.34 | 0.3318 | 323 |
| SEFA Soyate LP426 | 0.5793 | 441 | 0.3333 | 254 |
| ButterLean Olean | 0.4243 | 273.49 | 0.3488 | 225 |
| SEFA Soyate | 0.4603 | 227.49 | 0.3342 | 165 |
| Control (poloxamer/flavor only) | 0.3029 | 0 | 0.2881 | 0 |

Figure 1:
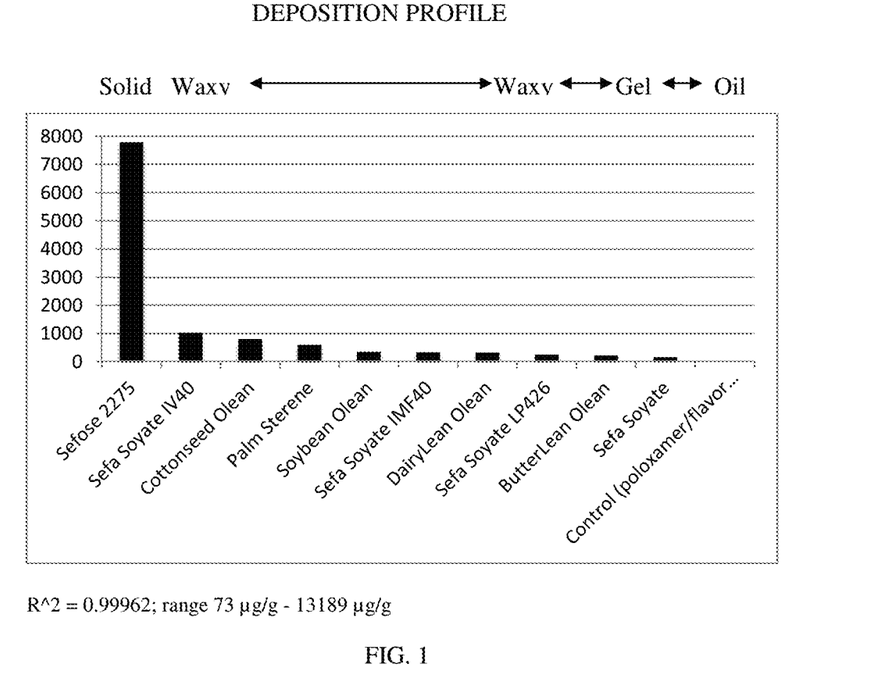
FIG. 1 is a graph showing deposition profile.

The deposition profile of the sucrose polyesters, as shown in FIG. 1 and TABLE 4, showed that Sefose 2275 had the highest deposition at 7785 µg/g of HAP, followed by SEFA Soyate IV40 at 1027 µg/g and then Cottonseed Olean at 800 µg/g. These three materials corresponded to the sucrose polyesters with the solid waxy profiles, as shown in FIG. 1. Those that were less waxy and a gel or oil-like, did not show as high of deposition. The amount of SPE deposition on the HAP particles correlates with tooth coating perception, as shown in TABLE 6 of EXAMPLE 2 below.

Example 2: Preference of Formulated Sucrose Polyesters

As shown in TABLE 5, dentifrice formulations containing Sucrose polyesters with differing deposition profiles, as shown in TABLE 4, were prepared using conventional methods, as described in U.S. Pat. No. 5,651,958, and provided to panelists for testing.

TABLE 5

| | Samples | | | | |
|---|---|---|---|---|---|
| Ingredient | A | B | C | D | E |
| Sodium Fluoride | 0.234% | 0.234% | 0.234% | 0.234% | 0.234% |
| Sorbitol | 38.00% | 38.00% | 38.00% | 38.00% | 38.00% |
| Silica | 15.0% | 15.0% | 15.0% | 15.0% | 15.0% |
| Titanium Dioxide | 0.53% | 0.53% | 0.53% | 0.53% | 0.53% |
| Carboxymethyl cellulose, sodium | 0.75% | 0.75% | 0.75% | 0.75% | 0.75% |

TABLE 5-continued

| Ingredient | Samples | | | | |
|---|---|---|---|---|---|
| | A | B | C | D | E |
| Tribasic sodium phosphate dodecahydrate | 1.10% | 1.10% | 1.10% | 1.10% | 1.10% |
| Sodium phosphate monobasic monohydrate | 0.42% | 0.42% | 0.42% | 0.42% | 0.42% |
| Carbomer 956 | 0.3% | 0.3% | 0.3% | 0.3% | 0.3% |
| Dye, F&DC Blue #1 color solution | 0.05% | 0.05% | 0.05% | 0.05% | 0.05% |
| Sodium Lauryl Sulfate, 28% solution | 4.00% | 4.00% | 4.00% | 4.00% | 4.00% |
| Sucrose Polyester | 1% Cottonseed Olean | 1% Palm Stearin | 1% Soybean | 1% Butterlean | 1% SEFA Soyate IMF40 |
| Water | QS | QS | QS | QS | QS |

*QS refers to the term quantum sufficit, meaning as much as suffices, where the remainder of the formula hole is filled with this substance.

The dentifrice formulations from TABLE 5 were provided to panelists for testing. There were three panelists used for each formulation. Each panelist brushed for two minutes with 1.5 grams of dentifrice on a generic toothbrush. They then expectorated and rinsed with tap water. After the rinse, they subjectively rated their preference among the samples, which were the most to least aesthetically pleasing, the tooth coating (from excellent to little or none), mouth/tooth feel (presence of "slick" feeling on tooth or other oral surface), and cooling/flavor profile (amount of cooling, onset of cooling, presence of good or bad flavor), as shown in Table 6. The mouth/tooth feel was ascertained by their perception of dragging their tongue across the forefront teeth and rating the drag/feel perception.

TABLE 6

| Preference | Sample | Coating | Mouth/Tooth Feel | Cooling/Flavor |
|---|---|---|---|---|
| Most preferred | A (Cottonseed Olean) | Excellent coating; | Very slick teeth | Cooling around gums, moderate flavor |
| Next Most preferred | B (Palm Stearin SFE) | Good coating | Smooth on teeth and lips | Delayed cooling. Low flavor |
| Moderate | C (Soybean) | Good coating | Moderate on cheeks not on tooth | Very intense delayed cooling. Low flavor |
| None | D (Butterlean) | Little | Little | Odd aftertaste. Good cooling. |
| None | E (SEFA Soyate IMF40) | Thick sample, little coating | None noticed | Little cooling and flavor non-existent. | n = 3, all sucrose polyesters's were formulated per TABLE 6 and tested for their coating profile.

Of the sucrose polyesters's tested, the Cottonseed Olean was the most preferred of the materials tested with the Palm Stearin next in preference, due to feel of the materials deposited on the teeth after brushing with a toothpaste containing them (Preference, Coating, Mouth/Tooth Feel, Cooling/Flavor). Of the sucrose's polyester dentifrice formulations tested in TABLE 6, the preferences followed the samples with the most deposition on HAP particles, as shown in TABLE 4, for example Cottonseed Olean had the most deposition with 800 µg/g and was the most preferred by the panelists, as shown in TABLE 6. The same was true with the other samples, namely those with higher levels of deposition (Palm Stearin SFE and Soybean), as shown in TABLE 4 and FIG. 1, were more preferred by panelists.

Example 3: Stain Prevention by Sucrose Polyester's

Hydroxyapatite powder (HAP) was used as a substrate in measuring stain prevention, as HAP was easily stained by tea and thus could be used to determine the level of stain prevention a sample may have. The HAP was pretreated, per the absorption studies in EXAMPLE 1, namely Hydroxyapatite (HAP, Biorad Bio-gel #130-0421) powder (1 g), was added to 50 ml conical centrifuge tube, which contained 20 ml of deionized water at room temperature (~68 F). The HAP water solution was vortexed for 30 seconds and then centrifuged for 15 minutes at 15,000 rpm to precipitate the washed HAP. The water was decanted and the procedure was repeated three more times. The pellet after the fourth wash was resuspended in 5-10 ml of deionized water and vortexed for 30 seconds. This solution was poured onto a Millipore filter disk (Millipore MF membrane filter 4.5 µm, 47 mm diameter, catalog #HAWP04700) in a vacuum filter apparatus. The disk was dried for two days at room temperature (25° C.). The powder was collected by scraping off the filter disk into a collection vial.

The sucrose polyester was directly formulated into a dentifrice, as described in EXAMPLE 2 and shown in TABLE 7. 20 g of the sucrose polyester formulation (if a dentifrice, it would be a 1:3 slurry in deionized water) was combined with the HAP in a centrifuge tube. Two tubes were left untreated as the control measures, one for the tea stain and one for the unstained HAP, which were run through the same washings as the treatments.

TABLE 7

| Ingredient | \multicolumn{10}{c}{Samples} | | | | | | | | | |
|---|---|---|---|---|---|---|---|---|---|---|
| | A | B | C | D | E | F | G | H | I | J |
| Flavor | 1.5% | 1.5% | 1.5% | 1.5% | 1.5% | 1.5% | 1.5% | 1.5% | 1.5 | 1.5 |
| Carrageenan | 0.7% | 0.7% | 0.7% | 0.7% | 0.7% | 0.7% | 0.7% | 0.7% | 0.7% | 0.7% |
| Zinc Lactate | 1% | 1% | 1% | 1% | 1% | 1% | 1% | 1% | 1% | 1% |
| Sodium Lauryl Sulfate, 28% solution | 5% | 5% | 5% | 5% | 5% | 5% | 5% | 5% | 5% | 5% |
| Carboxymethyl cellulose, sodium | 1.3% | 1.3% | 1.3% | 1.3% | 1.3% | 1.3% | 1.3% | 1.3% | 1.3% | 1.3% |
| Sorbitol | 33.4% | 33.4% | 33.4% | 33.4% | 33.4% | 33.4% | 33.4% | 33.4% | 33.4% | 33.4% |
| Silica | 15% | 15% | 15% | 15% | 15% | 15% | 15% | 15% | 15% | 15% |
| Stannous Fluoride | 0.454% | 0.454% | 0.454% | 0.454% | 0.454% | 0.454% | 0.454% | 0.454% | 0.454% | 0.454% |
| Hydroxyethyl cellulose (Med. Viscosity) | 1% | 1% | 1% | 1% | 1% | 1% | 1% | 1% | 1% | 1% |
| Gantrez S-95 | 5.71% | 5.71% | 5.71% | 5.71% | 5.71% | 5.71% | 5.71% | 5.71% | 5.71% | 5.71% |
| Sodium Gluconate | 1.06% | 1.06% | 1.06% | 1.06% | 1.06% | 1.06% | 1.06% | 1.06% | 1.06% | 1.06% |
| Cottonseed Olean | — | 1% | — | — | — | — | — | — | — | — |
| DairyLean Olean | — | — | 1% | — | — | — | — | — | — | — |
| Sefose 2275 | — | — | — | 1% | — | — | — | — | — | — |
| SEFA Soyate IV40 | — | — | — | — | 1% | — | — | — | — | — |
| SEFA Soyate LP 426 | — | — | — | — | — | 1% | — | — | — | — |
| Butterlean Olean | — | — | — | — | — | — | 1% | — | — | — |
| SEFA Soyate | — | — | — | — | — | — | — | 1% | — | — |
| Soybean Olean | — | — | — | — | — | — | — | — | 1% | — |
| SEFA Soyate IMF40 | — | — | — | — | — | — | — | — | — | 1% |
| Sodium Hydroxide solution, 50% | 1.3% | 1.3% | 1.3% | 1.3% | 1.3% | 1.3% | 1.3% | 1.3% | 1.3% | 1.3% |
| Water | QS | QS | QS | QS | QS | QS | QS | QS | QS | QS |

*QS refers to the term quantum sufficit, meaning as much as suffices, where the remainder of the formula hole is filled with this substance.

The staining consisted of steeping 1 bag of Lipton tea in 100 ml of hot water (50° C.) for 5 minutes. This tea was filtered through a Millipore 4.5 micron MF filter and kept at 50° C. The hot filtered tea (20 ml) was added to the HAP/treatment pellet. The HAP pellet was then prepped for image analysis by vortexing the pellet in 10 milliliters of deionized water for 30 seconds and then vacuum filtered onto the Millipore 4.5 micron disc. The discs were dried at room temperature (25° C.) for eight or more hours on a flat surface. The dried discs with HAP were laminated with clear heavyweight laminating sheets, such as C-Line products Inc., Mt. Prospect, Ill., laminating sheets. These laminated discs were then image analyzed using CIELAB color space software (Hyperterminal software package).

The term CIELAB is the second of two systems adopted by the CIE (Commission International de l'Eclairage) in 1976. This system is a coordinate space for assessing the color space originally developed by Richard Hunter in 1948. It is broken into three axes. The central axis is lightness (L*), where a positive value of 100 is pure white and a value of zero is complete black. One horizontal axis (b*) represents the shift from complete blue (−b) to complete yellow (+b). The second horizontal axis (a*) represents the shift from complete green (−a) to complete red (+a). The zero intersection point of all three axes is the neutral gray. The delta values (ΔL, Δa, and Δb) depict how far away from a standard the measured value is.

Figure 2:
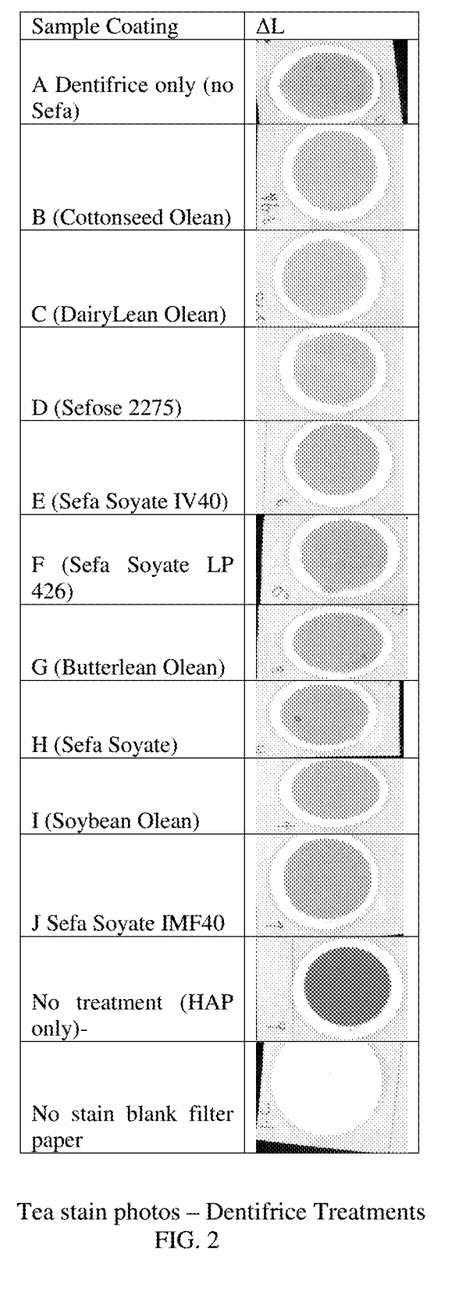
FIG. 2 is a photograph demonstration of stain.

The level of HAP staining, as shown in FIG. 2, relative to the untreated tea control, was used to measure the level of stain prevention a specific chemistry had. This difference was quantified with image analysis according to the protocol outlined below and reported as CIELAB numbers.

TABLE 8

| Dentifrice | ΔL | Δa | Δb | ΔE |
|---|---|---|---|---|
| Dentifrice only (no SPE) | −15.76 | 7.96 | 12.98 | 21.93 |
| B (Cottonseed Olean) | −12.40 | 7.10 | 9.43 | 17.12 |
| C (DairyLean Olean) | −11.97 | 7.05 | 10.26 | 17.28 |
| D (Sefose 2275) | −12.26 | 6.99 | 10.44 | 17.56 |
| E (SEFA Soyate IV40) | −14.84 | 8.11 | 11.30 | 20.34 |
| F (SEFA Soyate LP 426) | −16.64 | 7.71 | 10.33 | 21.05 |
| G (Butterlean Olean) | −16.27 | 8.09 | 10.72 | 21.10 |
| H (SEFA Soyate) | −16.31 | 8.18 | 10.82 | 21.21 |
| I (Soybean Olean) | −15.65 | 7.74 | 12.63 | 21.55 |
| J containing SEFA Soyate IMF40 | −16.16 | 8.41 | 12.95 | 22.35 |
| HAP only (no SPE) | −30.56 | 11.45 | 15.44 | 36.13 |

The results shown in TABLE 8 demonstrated that the dentifrice containing Sefose 2275, Cottonseed Olean, SEFA soyate IV40, or DairyLean Olean caused a reduction in stain, as illustrated by their lower ΔE values as compared to the dentifrice with no sucrose polyester.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tooth coating composition comprising sucrose polyester that is at least one of Cottonseed Olestra, Sucrose Ester Fatty Acid (SEFA) Behenate, or Sucrose Ester Fatty Acid (SEFA) Soyate IV40;
   wherein the tooth coating composition has a sucrose polyester deposition measurement of at least about 500 μg/g of hydroxyapatite (HAP), as measured by the HAP particle deposition method.

2. The oral care composition of claim 1, wherein the tooth coating composition has a HAP particle absorption rate of about 55% or less for deionized water.

3. The tooth coating composition of claim 1, wherein the tooth coating composition has a HAP particle deionized water flow rate of about 35% or greater.

4. The tooth coating composition of claim 1, wherein the tooth coating composition has a lower tea stain ΔE value when applied to a HAP surface as compared to an untreated HAP surface.

5. The tooth coating composition of claim 1, wherein the tooth coating composition has a tea stain ΔE when applied to a HAP surface of about 21 or less.

6. The tooth coating composition of claim 5, wherein the tooth coating composition has a tea stain ΔE when applied to a HAP surface of about 18 or less.

7. The tooth coating composition of claim 1, wherein the sucrose polyester has a solids fat content of at least about 40% at 10° C.

8. The tooth coating composition of claim 1, wherein the sucrose polyester has a solids fat content of at least about 40% at 10° C. and at least 5% at 40° C.

9. A tooth coating composition comprising a sucrose polyester that is at least one of Cottonseed Olestra, Sucrose Ester Fatty Acid (SEFA) Behenate, or Sucrose Ester Fatty Acid (SEFA) Soyate IV40, wherein the tooth coating composition has
   a HAP particle absorption rate of about 55% or less for deionized water
   and a HAP particle deionized water flow rate of about 35% or greater;
   wherein the sucrose polyester has a solids fat content of at least about 40% at 10° C.; and
   wherein the tooth coating composition has a sucrose polyester deposition measurement of at least about 500 μg/g of HAP, as measured by the HAP particle deposition method.

10. The tooth coating composition of claim 9, wherein the tooth coating composition has a lower tea stain ΔE value when applied to a HAP as compared to an untreated HAP particle.

11. The tooth coating composition of claim 10, wherein the tooth coating composition has a tea stain ΔE when applied to a HAP surface of about 21 or less.

12. The tooth coating composition of claim 11, wherein the tooth coating composition has a tea stain ΔE when applied to a HAP surface of about 18 or less.

13. The tooth coating composition of claim 9, wherein the sucrose polyester has a solids fat content of at least about 40% at 10° C. and at least 5% at 40° C.

* * * * *